(12) United States Patent
Lochte et al.

(10) Patent No.: US 7,857,800 B2
(45) Date of Patent: Dec. 28, 2010

(54) TAMPON HAVING APERTURED FILM COVER THERMOBONDED TO FIBROUS ABSORBENT STRUCTURE

(75) Inventors: Karin Lochte, Wuppertal (DE); Lai-Hing Louie, Kendall Park, NJ (US); Sharon Ryan, Pennington, NJ (US); Hans-Werner Schoelling, Ennepetal (DE)

(73) Assignee: Johnson & Johnson GmbH, Dusseldorf (DE)

( * ) Notice: Subject to any disclaimer, the term of this patent is extended or adjusted under 35 U.S.C. 154(b) by 321 days.

(21) Appl. No.: 11/453,486

(22) Filed: Jun. 15, 2006

(65) Prior Publication Data

US 2006/0241556 A1 Oct. 26, 2006

Related U.S. Application Data

(63) Continuation of application No. 10/896,697, filed on Jul. 21, 2004, now abandoned.

(60) Provisional application No. 60/141,688, filed on Jun. 30, 1999.

(51) Int. Cl.
*A61F 13/15* (2006.01)
(52) U.S. Cl. .................. 604/385.18; 604/904
(58) Field of Classification Search ............ 604/385.18, 604/904
See application file for complete search history.

(56) References Cited

U.S. PATENT DOCUMENTS

| | | |
|---|---|---|
| 1,703,811 A | 2/1929 | Blum |
| 1,707,400 A | 4/1929 | Kerruish |
| 2,518,785 A | 8/1950 | Houk |
| 2,793,585 A | 5/1957 | Granitsas |
| 2,943,428 A | 7/1960 | Stroop |
| 2,958,366 A | 11/1960 | Conti |
| 3,015,996 A | 1/1962 | Ambler et al. |
| 3,153,607 A | 10/1964 | Ambler |
| 3,346,438 A | 10/1967 | Chavannes |
| 3,430,506 A | 3/1969 | Stone |
| 3,547,743 A | 12/1970 | Tunner |
| 3,558,400 A | 1/1971 | Horvath et al. |
| 3,588,400 A | 6/1971 | Horvath et al. |
| 3,888,241 A | 6/1975 | Fischer |

(Continued)

FOREIGN PATENT DOCUMENTS

DE 1 560 128 A 2/1971

(Continued)

*Primary Examiner*—Tatyana Zalukaeva
*Assistant Examiner*—Lynne Anderson

(57) ABSTRACT

A tampon having an absorbent structure and an apertured film cover thermally bonded to the absorbent structure is disclosed. The cover is bonded to the absorbent structure through a plurality of discrete spots arranged about the surface of the absorbent structure to provide a cumulative cover-to-absorbent bond. The cumulative cover-to-absorbent bond has a shear strength of at least about 3 N. The plurality of discrete thermally-bonded spots define a bonded area and the bonded spots and the unbonded portions between the spots define a bond region. Preferably, the bonded area covers about 5% to about 30% of the bond region.

In addition, a sealing element for a sealing roller is disclosed. The sealing element is profiled with a sealing pattern defined by sealing knobs arranged at distances to each other that project from a base of the sealing element. Each sealing knob has a perimeter shaped to eliminate aggressive edges.

6 Claims, 4 Drawing Sheets

U.S. PATENT DOCUMENTS

| | | | |
|---|---|---|---|
| 3,929,135 A | 12/1975 | Thompson | |
| 4,100,324 A | 7/1978 | Anderson et al. | |
| 4,436,576 A | 3/1984 | Seiden | |
| 4,475,911 A * | 10/1984 | Gellert | 604/367 |
| 4,695,422 A | 9/1987 | Curro et al. | |
| 4,741,877 A | 5/1988 | Mullane, Jr. | |
| 4,816,100 A | 3/1989 | Friese | |
| 4,889,271 A | 12/1989 | Kurokawa | |
| 5,042,383 A | 8/1991 | Wirz | |
| 5,131,383 A | 7/1992 | Juarez | |
| 5,264,268 A | 11/1993 | Luceri et al. | |
| 5,326,612 A | 7/1994 | Goulait | |
| 5,403,300 A | 4/1995 | Howarth | |
| 5,567,376 A | 10/1996 | Turi et al. | |
| 5,591,149 A | 1/1997 | Cree et al. | |
| 5,621,969 A | 4/1997 | Masuda | |
| 5,634,914 A | 6/1997 | Wilkes et al. | |
| 5,755,906 A * | 5/1998 | Achter et al. | 156/217 |
| 6,231,555 B1 * | 5/2001 | Lynard et al. | 604/385.01 |
| 6,433,246 B1 * | 8/2002 | Nguyen et al. | 604/375 |
| 6,465,713 B1 * | 10/2002 | Gell et al. | 604/383 |
| 6,537,414 B1 | 3/2003 | Schoelling | |
| 6,874,394 B1 | 4/2005 | Ryan et al. | |

FOREIGN PATENT DOCUMENTS

| | | |
|---|---|---|
| EP | 0 295 957 A | 12/1988 |
| EP | 0 456 281 A | 11/1991 |
| EP | 0 738 505 A | 10/1996 |
| EP | 0 841 156 A | 5/1998 |
| JP | 1-195867 A | 8/1989 |
| WO | WO 97/23185 A | 7/1997 |
| WO | WO 98/20825 A | 5/1998 |
| WO | WO 98/46182 A | 10/1998 |
| WO | WO 99/00096 A | 1/1999 |
| WO | WO 99/26769 A | 6/1999 |
| WO | WO 01/01903 A1 | 1/2001 |
| WO | WO 01/01910 A1 | 1/2001 |

* cited by examiner

TAMPON HAVING APERTURED FILM COVER THERMOBONDED TO FIBROUS ABSORBENT STRUCTURE

CROSS-REFERENCE TO RELATED APPLICATIONS

This application is a continuation of U.S. application Ser. No. 10/896,697, filed Jul. 21, 2004, now abandoned which claims priority to 60/141,688 filed Jun. 30, 1999. The complete disclosure of the aforementioned related US patent application is hereby incorporated herein by reference for all purposes.

CROSS-REFERENCE TO RELATED APPLICATIONS

This application is related to the following copending applications: U.S. Ser. No. 09/343,759; U.S. Ser. No. 09/345,090; U.S. Ser. No. 09/345,089; U.S. Ser. No. 09/343,760; U.S. Ser. No. 09/345,088; U.S. Ser. No. 60/141,688, and U.S. Ser. No. 60/141,690; all filed on Jun. 30, 1999, and to U.S. Ser. Nos. 10/303,261 and 10/586,019 filed on even date herewith, entitled "Sealing Roller And Sealing Roller Element Particularly For Producing A Tampon For Feminine Hygiene And Method Therefor" and "Tampon For Feminine Hygiene And Process and Apparatus For Its Production", respectively.

FIELD OF THE INVENTION

The invention relates to a tampon, preferably for feminine hygiene, having an apertured film cover thermobonded to an absorbent structure, as well as a method for producing such a tampon.

BACKGROUND OF THE INVENTION

Friese, U.S. Pat. No. 4,816,100 discloses a method and a device for producing a tampon for the feminine hygiene. The method provides a fluid permeable and at least partially thermoplastic wrapping material being divided into sections which is applied onto a fleece web by heat sealing. Fleece web sections that are severed from the fleece web are wound onto themselves to form a tampon blank having a withdrawal cord. Thereby the fluid permeable wrapping material is positioned on the circumference of the tampon blank and substantially surrounds it. Finally, the tampon blank is pressed radially into the final shape of the tampon.

While this was an advance for tampon technology at the time, there has been recent interest in using apertured film covers on tampons. These covers present additional problems in secure attachment, especially through heat sealing. For example, the heat sealing may close the apertures in the otherwise liquid impermeable plastic film.

Therefore, what is needed is a tampon having an apertured film cover securely fastened to its absorbent structure without adversely affecting the absorbent characteristics of the tampon.

SUMMARY OF THE INVENTION

A tampon having an absorbent structure and an apertured film cover thermally bonded to the absorbent structure is disclosed. The cover is bonded to the absorbent structure through a plurality of discrete spots arranged about the surface of the absorbent structure to provide a cumulative cover-to-absorbent bond. The cumulative cover-to-absorbent bond has a shear strength of at least about 3 N. The plurality of discrete thermally-bonded spots define a bonded area and the bonded spots and the unbonded portions between the spots define a bond region. Preferably, the bonded area covers about 5% to about 30% of the bond region.

In addition, a sealing element for a sealing roller is disclosed. The sealing element is profiled with a sealing pattern defined by sealing knobs arranged at distances to each other that project from a base of the sealing element. Each sealing knob has a perimeter shaped to eliminate aggressive edges.

BRIEF DESCRIPTION OF THE INVENTION

DETAILED DESCRIPTION OF THE PREFERRED EMBODIMENT

As used herein, the term "apertured film" refers to a fluid-impervious plastic material in the form of a resilient three-dimensional web having first and second surfaces and exhibiting a fiber-like appearance and tactile impression. The first surface of the three-dimensional web has a multiplicity of apertures therein.

Preferably, each of the apertures is defined by a multiplicity of intersecting, fiber-like elements interconnected to one another substantially in the plane of the first surface. Each of the fiber-like elements exhibits a cross-section, preferably having a base portion in the plane of the first surface and a sidewall joined to each edge of the base portion. The sidewall portions extend generally in the direction of the second surface of the three-dimensional web. Further, the intersecting sidewall portions are interconnected to one another intermediate the first and second surfaces of the web. The interconnected sidewall portions preferably terminate substantially concurrently with one another in the plane of the second surface.

As used herein, the term "cover" refers to an element of an absorbent article that, alone or in conjunction with one or more additional element(s), substantially encloses an absorbent structure. The term especially refers to such an element located on the outer surface of a tampon.

Figure 1:
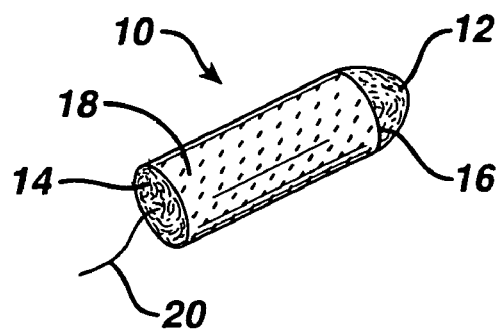
FIG. 1 is a perspective view of a tampon according to the present invention.
Figure 2:
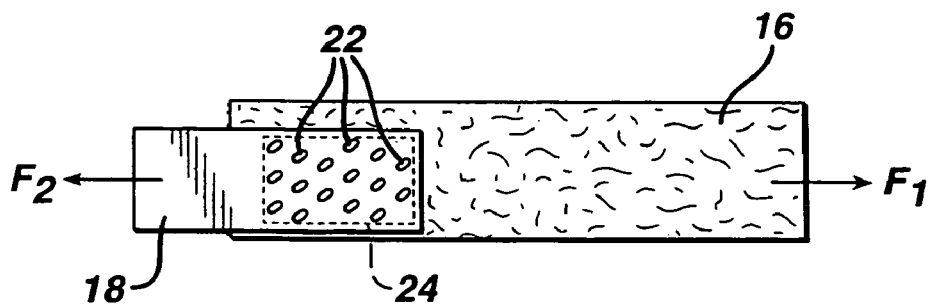
FIG. 2 is a plan view of an absorbent web having an apertured film cover attached thereto through a pattern of discrete, thermally bonded spots.
Figure 3:
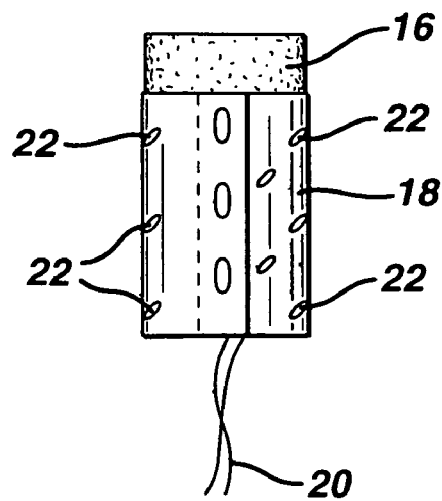
FIG. 3 is a side elevation of a spirally wound tampon blank having an apertured film cover attached to itself.

A tampon having an apertured film cover is illustrated in FIG. 1. This tampon 10 has an insertion end 12 and a trailing end 14, and it is formed of an absorbent structure 16 substantially covered by an apertured film material or cover 18. In addition, a withdrawal string 20 extends from the trailing end 14 of the tampon 10.

The absorbent structure may be any absorbent means that is capable of absorbing and/or retaining liquids (e.g., menses). The absorbent structure can be manufactured in a wide variety of sizes and shapes and from a wide variety of liquid-absorbing materials. A representative, non-limiting list of useful materials includes cellulosic materials, such as rayon, cotton, wood pulp, creped cellulose wadding, tissue wraps and laminates, peat moss, and chemically stiffened, modified, or cross-linked cellulosic fibers; polymeric materials, such as polyester fibers, polyolefin fibers, absorbent foams, absorbent sponges, superabsorbent polymers, absorbent gelling materials; formed fibers, such as capillary channel fibers and multilimbed fibers; combinations of materials, such as synthetic fibers and wood pulp including coformed fibrous structures (e.g., those materials described in Anderson et al., U.S. Pat. No. 4,100,324); or any equivalent material or combinations of materials, or mixtures of these. Preferably, the absorbent structure comprises one or more elements to provide it with structural integrity. This structural integrity allows the absorbent structure to be securely attached to the cover. Representative, non-limiting examples of elements that provide structural integrity include fibrous webs, films, and the like.

The cover of the present invention can be manufactured by standard processes known to those of ordinary skill in the art. For example, the base film that is to be apertured can be extruded, cast, or blown to form the film. The base film can be a single formulated polymeric material or blend, or it can be a laminated or multi-layered material such as described in commonly assigned, co-pending applications to Johnson et al., U.S. Ser. No. 09/345,090, and Gell et al., U.S. Ser. No. 09/345,089, the disclosures of which are herein incorporated by reference. Useful technology to form these films will be easily recognized by those of ordinary skill in the art. The base film can then be apertured by any useful process. Several examples include hot air aperturing, and water jet aperturing. Examples of these processes are disclosed in Curro, U.S. Pat. No. 4,695,422; Turi, U.S. Pat. No. 5,567,376; and Mullane, U.S. Pat. No. 4,741,877; the disclosures of each of these patents are hereby incorporated by reference. The resulting apertured film can be coated, for example as described in commonly assigned, co-pending application U.S. Ser. No. 09/345,088, filed Jun. 30, 1999, entitled "Tampon with Cover and Nonionic Surfactant", and/or slit to a desired width for use in manufacturing a tampon.

The cover 18 is useful to contain the absorbent structure materials to reduce, preferably prevent, the likelihood that any significant portion of the absorbent structure 16 will escape from the tampon 10 and remain after the tampon 10 has been removed, e.g., by pulling on the withdrawal string 20. The cover 18 can also protect the tissue in contact with the tampon 10 from excessive friction or other irritation during insertion, use, and removal of the tampon 10. Further, the cover 18 can add aesthetic qualities to the tampon 10. Therefore, it is desirable that the cover 18 have the following properties low coefficient of friction, smooth surface, high opacity, clear apertures, and an unmelted appearance.

Because the cover 18 contains the absorbent structure 16, and the cover 18 and absorbent structure 16 should be secured to each other, the cover 18 should be capable of thermally bonding at least to itself in a manner that secures the absorbent structure 16 within it. In addition, the cover 18 is also capable of thermally bonding to the outer portions of the absorbent structure 16, itself.

The apertured film cover 18 is attached to the absorbent structure 16 through a plurality of discrete, thermally bonded spots 22. These spots 22 are arranged to provide thermal bonds having relatively small area over a relatively large surface of the tampon 10. The area of the thermal bonds can be aggregated to provide a bonded area, and the bonded spots and the unbonded portions between the spots together define a bond region 24. The bonded area covers about 5% to about 30% of the bond region, preferably about 10% to about 25% of the bond region 24, and more preferably, about 15% to about 20% of the bond region 24.

This amount of coverage of the bond region is less than the coverage obtained in the prior art, e.g., Friese, U.S. Pat. No. 4,816,100. A commercial example of Friese, the O.B.® tampon has a sealing pattern of continuous diagonal lines covers about 40% of its bond area.

The plurality of discrete, thermally bonded spots 22 cooperates to provide a cumulative cover-to-absorbent bond. This bond is of sufficient strength to maintain the integrity of the covered tampon during manufacture, storage, and use. A measure of this bond can be made by determining the shear force required to separate the cover from the absorbent structure. The method to determine this strength is described below. The cumulative cover-to-absorbent bond is at least about 3 N. This shear strength provides sufficient strength to maintain the reassure a user that the cover will remain associated with the absorbent structure during use, especially during removal. Preferably, the cover-to-absorbent shear strength is at least about 2 N, and more preferably, the shear strength of the bond is about 3 N to about 10 N.

One method of applying the apertured film cover material to an absorbent structure in the manufacture of a tampon is the use of a cut-and-place unit to cut the material from the slit roll and to place it on the absorbent structure. Another method is generally described in Friese, U.S. Pat. No. 4,816,100, the disclosure of which is herein incorporated by reference.

While this describes the application of a nonwoven cover to a tampon, improvements necessary to achieve this are described in the commonly-assigned, copending application, U.S. Ser. No. 09/343,759, filed Jun. 30, 1999, entitled "Continuous Method of Providing Individual Sheets from a Continuous Web", the disclosure of which is herein incorporated by reference. This copending application discloses a method to achieve the total separation of a section of material comprising the following steps: severing a supply material in a plurality of discrete regions along a transverse axis, scoring the material residing between the severed regions along the same transverse axis, and then applying a force sufficient to fracture the scored regions, thereby separating the section of material from its supply. The section of material provides the cover of the present invention, and as disclosed in Friese, this cover can be thermally bonded to a nonwoven absorbent web.

Figure 4:
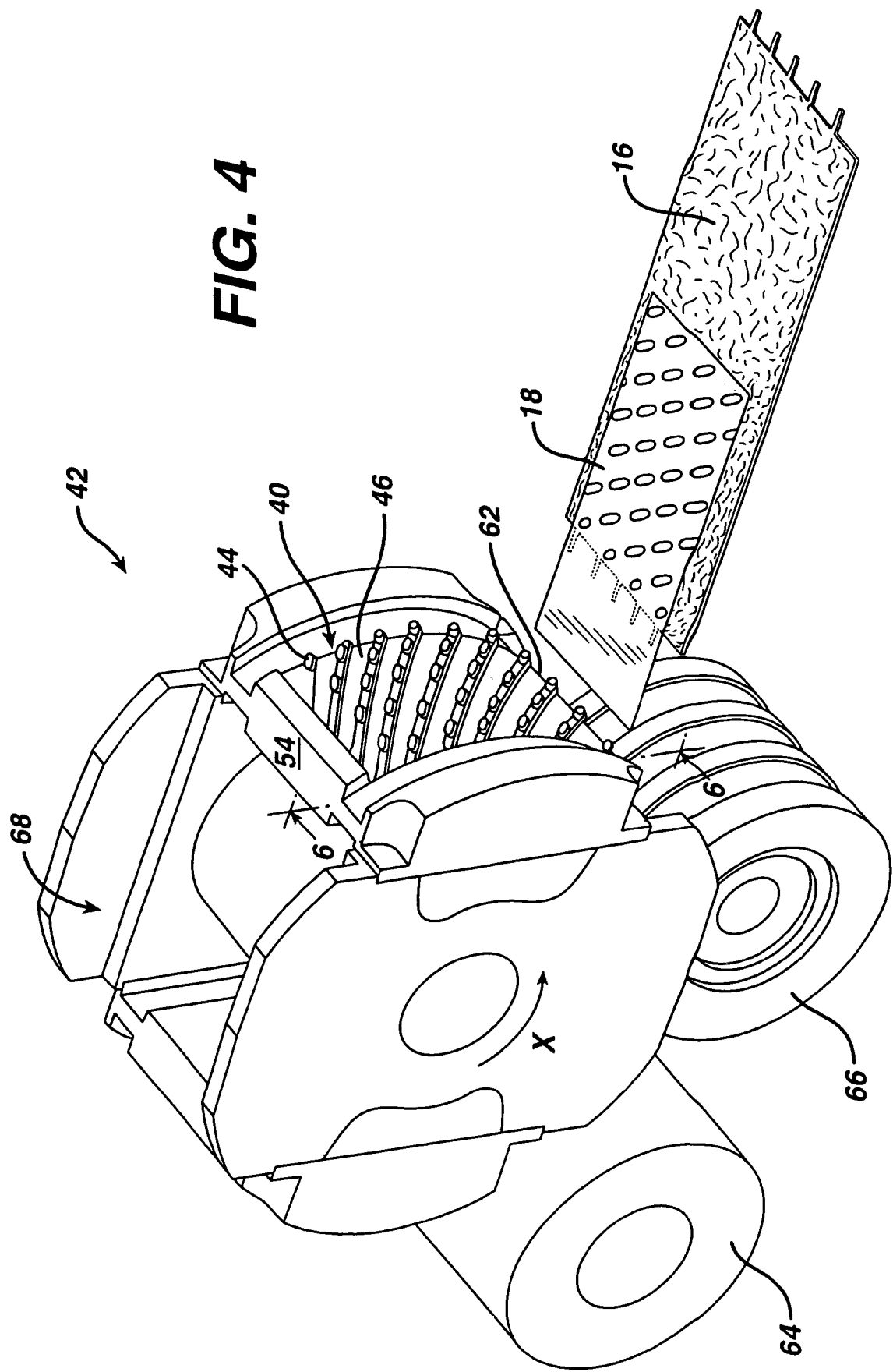
FIG. 4 is a perspective view of a sealing roller useful in manufacturing a tampon according to the present invention.

The thermal bonding is preferably achieved through the use of a sealing element 40 of a sealing roller 42 that is profiled by a sealing pattern (shown in FIG. 4).

According to the invention, the sealing pattern is formed by sealing knobs 44 or projections that project from a base 46 of the sealing element 40. Preferably, the sealing knobs 44 have rounded edges 48 or edges 48 having an outer angle α (as shown in FIG. 5) formed between the sealing surface 50 of a sealing knob 44 that contacts and compresses the cover and knob sidewalls 52.

Preferably the outer angle α is more than 180° and up to about 240°. This sealing element 40 reliably prevents damage to the cover that would impair the function of the tampon as well as its appearance. As no acute-angled edges 48 are applied to the cover 18, the pressure and temperature applied by the sealing element 40 to the cover 18 may be much higher than a prior art sealing element without causing injury or damage to the cover material 18.

It is preferred to avoid sharp edges or overhangs on the sealing knobs 44. The preferred outer contours of a sealing knob 44 according to the invention are smoothly rounded from the sealing surface 50 to the knob sidewalls 52. The sealing surface 50 of the knobs 44 may have any desired general shape to provide such shape to the thermally sealed spots. For example, the sealing surface 50 may be generally circular, ellipsoid, polygonal, and curvilinear combinations thereof. Preferably, the sealing surface 50 is substantially circular, oval, or ellipsoid to minimize the danger of damage or injury to the cover material to be sealed. Most preferably, the sealing surface is substantially oval (or rectangular having substantially hemispherical ends). These contours also provide reliable thermal bonding between cover and the absorbent structure, even if the system, as intended, is exposed to humidity.

In a preferred embodiment, the sealing knobs 44 are arranged on the sealing element 40 in diagonal spaced apart rows. The arrangement of the sealing knobs 44 on the sealing element 40 may be varied for visual reasons. The dimension and arrangement of the sealing knobs may be chosen as desired. However the distance "d" between the adjacent sealing knobs should not be too great or reliable contact between cover 18 and absorbent structure 16 section may not occur. In addition, it is possible that the knobs 44 form defined signs or have a meaning when combined. At least the front end 54 of the sealing element 40 when seen in the direction of rotation "x" is preferably equipped with sealing knobs 44 in its edge 56 and end 58 areas. This location of knobs 44 will help to prevent undesired movement of the cover material 18 and to securely attach the cover 18 to the absorbent structure 16.

The preferred oval-surfaced sealing knobs 44 have a length of about 5.5 mm and a width of about 3 mm. With the rounded ends and contours, this can produce a sealing knob with an individual sealing surface area of about 14.7 mm$^2$. However, it is preferred that each individual sealing surface has an area of less than about 40 mm$^2$, more preferably, less than about 25 mm$^2$ and most preferably between about 5 and 15 mm$^2$. This sealing surface will provide a corresponding surface area for each thermally bonded spot in the cover/absorbent structure.

Preferably, adjacent sealing knobs 44 are not separated by a distance "d" of more than about 2 mm, more preferably, adjacent sealing knobs are within about 3 mm to about 15 mm, and most preferably, within about 5 mm to about 10 mm. Of course, the location of the sealing knobs 44 determines a corresponding spacing of the thermally bonded spots 22 on the tampon blank and the finished tampon product.

Generally, the sealing knobs 44 are uniformly distributed about the sealing element 40. However, it may be helpful to decrease spacing between them at edge regions of the sealing element 40 to securely fasten the periphery of the cover material 18 to the absorbent structure 16.

Preferably, the sealing knobs 44 are arranged in a pattern aligned at an angle oblique to the circumference of the sealing roller 42. This is especially noticeable when the sealing knobs 44 have a more rectangular or oval shape. This angle allows the flow of liquid along the surface of the tampon to be deviated from a line directly along the length of the tampon. This has two effects: first, the distances the liquid can flow at the surface of the tampon is increased due to the deviation from a straight line along the tampon. This increases the likelihood that the liquid will be absorbed. Second, the discrete thermally bonded spots 22 do not provide a direct line of flow along the tampon. This increases the fluid dwell time on the surface to allow the underlying absorbent structure to draw it into the tampon. This can provide for improved specific absorption areas around the bonded spots to improve the overall absorption of the tampon.

There may be a number of lines of sealing knobs 44 viewed across the sealing element 40. In a preferred embodiment, there may be about 2 to about 10 lines across the face of the sealing element 40, more preferably about 3 to about 7, and most preferably, about 3 to about 5 lines of sealing knobs 44.

In this arrangement, the sealing knobs 44 may be staggered such that there are fewer sealing knobs 44 bonding the cover to the absorbent structure than there are lines of knobs 44. This allows the increased pressure exerted onto the cover/absorbent structure with the same force in comparison to the continuous line of the prior art O.B.® products. The same force used in the prior art products can be applied to a smaller area to provide a greater bonding pressure and to increase the overall integrity of the cover-to-absorbent bond.

The discrete thermally bonded spots 22 are optimally bonded in a manner that the apertures in the cover material are not significantly closed and the thermally bonded spots 22 are capable of transmitting fluid through the apertures of the cover 18 within the thermally bonded spots 22. The sealing elements 10 are made of a thermally conductive material. A representative, non-limiting list of materials includes metals such as steel, including stainless steel, mild steel, tool steel, and the like; and aluminum. Useful stainless steels include the 300 series including 303, 304, and 316; the 400 series, and the 800 series. Useful mild steels include 1018 and 1020. Useful aluminum alloys include the 2000 series including 2024; the 3000 series including 3003; the 5000 series including 5052 and 5080; the 6000 series including 6061, 6063, and 6082; and the 7000 series including 7075. These materials can be coated with appropriate coatings to protect the sealing element from corrosion and wear and to reduce the likelihood of the sealed material from adhering to the tooling surfaces. Such materials will be recognized by those of ordinary skill in the art.

Heating elements are associated with the sealing elements 40 in a manner to provide well-controlled heat to the sealing knobs 44. Preferably, the heating elements controllable to provide a heat accuracy of +/−5° C., more preferably, about +/−2° C. This can be achieved by placing, e.g., two heating elements symmetric to a middle plane of the sealing element 40, or three or more elements in appropriate locations on the sealing element. Alternatively, it is possible to employ a single plate heating element or to incorporate conduits within the sealing element 40 to accommodate a circulated heating fluid. In addition, a temperature control element, such as a thermocouple, can be provided close to the sealing surfaces, e.g., at the middle plane of the sealing element 40.

Figure 6:
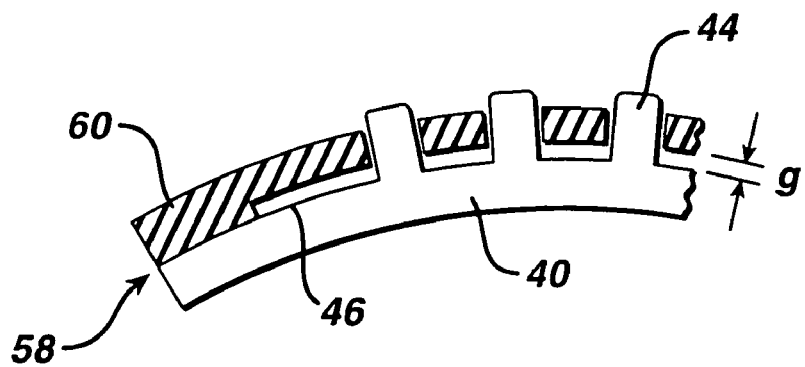
FIG. 6 is a partial cross-section of the sealing element taken along line 6-6 in FIG. 4.

In addition to the sealing knobs 44, the sealing element preferably includes a thermal insulating material 60 in the portions of the sealing element 40 surrounding and between the sealing knobs 44 as shown in FIG. 6. This insulating material 60 may be any thermal insulating material that is effective at the operating temperature of the sealing or bonding process. A representative, non-limiting list of possible insulating materials include elastomeric materials, such as latex rubber, silicone rubber, elastomeric block copolymers and the like; and high temperature plastics based upon polytetrafluoroethyelene (PTFE) known as "PEEK" according to the European DIN norm; and the like. Preferably, the insulating material is medically approved and elastomeric, or at least resilient, more preferably, the insulating material is a high temperature plastic such as one having a glass transition temperature of at least about 140° C. such as fiber reinforced materials including the TECAPEEK materials available from Ensinger GmbH & Co., Nufringen, Germany. The insulating material 60 is preferably in contact with the base 46 of the sealing element 40 at the leading 58 and trailing ends 62 of the sealing element 40 when viewed according to the direction of rotation "x", but it may be separated by small gap "g" intermediate these ends. The gap will generally be less than about 1 mm, more preferably, the gap is about 0.2 mm to about 0.7 mm, and most preferably, the gap is about 0.5 mm. This gap allows for some minor movement of the insulating material accounting for the fleece web thickness that passes in the nip between the sealing element 40 and, e.g., a pressure roller 64. The pressure faced by the fleece web in this nip helps to calender the fleece web to maintain a relatively uniform density during processing.

The insulating material 60 preferably has a thickness of about 1 mm to about 4 mm, more preferably about 2 mm. The insulating material 60 may be substantially of uniform thickness (excluding, of course the holes necessary to allow the sealing knobs 44 to project therethrough) as discussed above, or one or more recesses may be formed in it. For example, a substantially rectangular recess 61 may be formed in the surface of the insulating material 60 facing the base 46 of the sealing element 40. The recess 61 may increase the flexibility of the insulating element 60, and it can serve as a spring element to help to provide a substantially uniform pressure to the cover/absorbent structure. The recess 61 may have a depth of about 10% to about 50% of the thickness of the insulating material 60.

The sealing knobs 44 preferably project from the base 46 of the sealing element 40 and extend above the insulating material 60 by at least about 1 mm, preferably by about 3 mm to about 7 mm, and most preferably by about 5 mm.

The invention further relates to a method for producing a tampon for feminine hygiene. In particular, it relates to a method involving thermally bonding an at least partially thermoplastic cover material to an absorbent structure at a desired temperature.

The preferred bonding temperature is 140° C. for a preferred fleece web containing cotton and rayon or rayon blends and an apertured film cover material containing polyethylene. This provides a reliable heat sealing of the materials in use. The cover material is reliably bonded with the fleece web section in the desired bond region while the rest of the cover material attains a temperature that does not cause it to bond or otherwise be damaged.

FIG. 4 shows a perspective view of a sealing roller as well as a fleece web section 16 with a cover 18 sealed onto it. The sealing elements 40 comprise sealing knobs 44 arranged in transverse rows and at distances from one another with said sealing knobs projecting about 0.3 cm from a base 46 of the sealing elements 40.

Figure 4A:
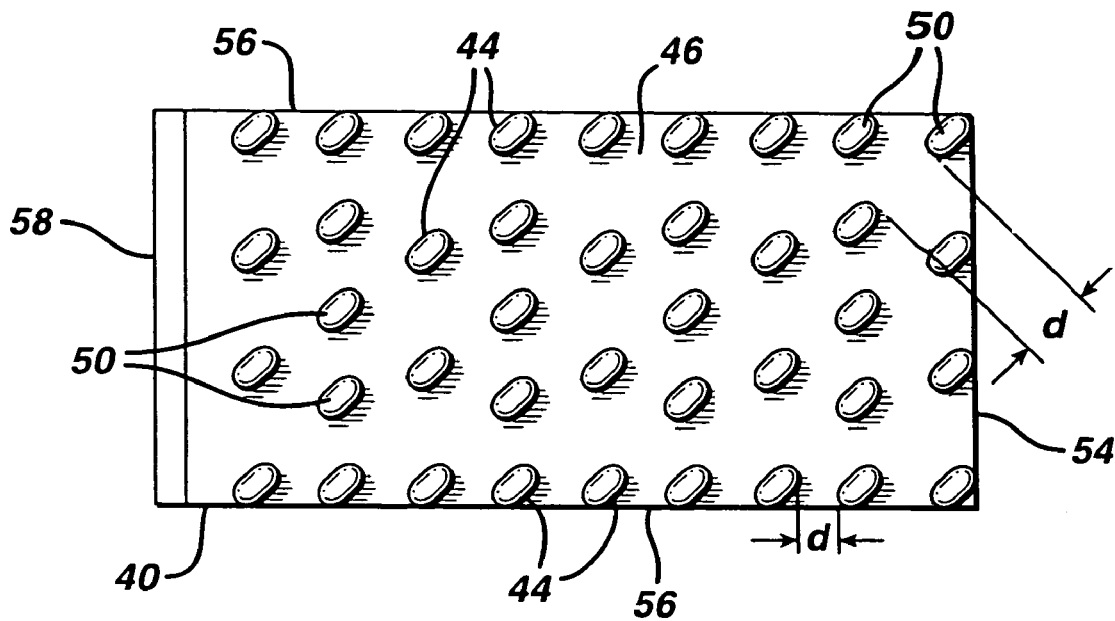
FIG. 4A is a plan view taken along the circumference of the sealing element of FIG. 4.

According to FIGS. 4 and 4A, the sealing knobs 44 have a substantially oval and rounded off sealing surface 50. The transition from each sealing surface 50 to the knob sidewalls 52 is substantially vertical to the base 46 of the sealing elements 40. Therefore, the parts of the sealing knobs 44 being in contact with the fleece web section 16 and/or the cover material 18 do not have sharp edges.

The pressure roller 64 presses the fleece web 16 against the sealing roller 42 so that the wrapping material 18 is securely sealed onto the fleece web by sealing elements 40. Furthermore, it is provided for another transport and/or driving roller 66 that drives the fleece web 16 and/or holds it in the desired position.

In operation the sealing elements 40 are preferably heated up to a temperature of 140° C. This preferably results in a surface temperature of the sealing surface 52 also of about 140° C.

Optional elements consisting of the remaining segments of the sealing roller cylinder can be inserted into the sealing roller 42 in the voids 68. These elements may be ironing elements described in U.S. Ser. No. 10/303,261, filed on even date herewith, entitled "Sealing Roller And Sealing Roller Element Particularly For Producing A Tampon For Feminine Hygiene And Method Therefor", the disclosure of which is herein incorporated by reference.

FIG. 5 shows diagrammatically in cross-section various embodiments of the sealing knobs 44 of the sealing element 140.

Figure 5A:
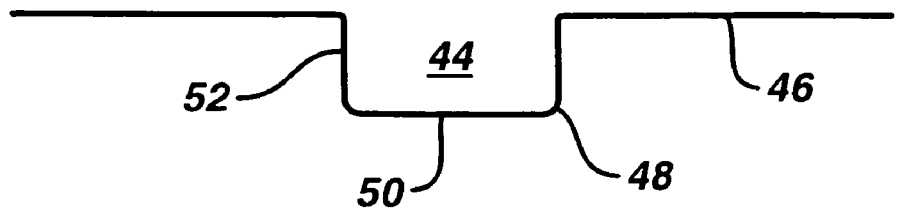
FIGS. 5A-5C are cross-sections of various sealing knobs of the sealing element of FIG. 4.

Sealing knob 44 shown in FIG. 5a comprises a substantially smooth sealing surface 50 and smooth knob sidewalls 52 substantially vertically arranged with respect to the sealing surface 50 so that the sealing knobs 44 are substantially square. The edges between the sealing surface 50 and the knob sidewalls 52 are rounded off. Such rounding off is not provided for at the edges between the knob sidewalls 52 and the base 46 of the sealing element, since these regions are not in contact with the fleece web 100, the fleece web section 105 or the wrapping material 200 while the sealing roller 42 is in operation.

Figure 5B:
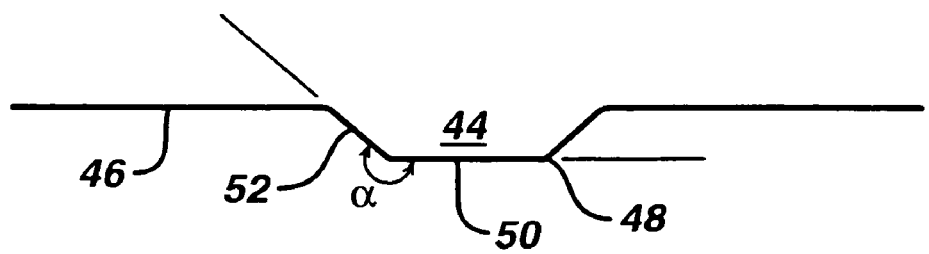

FIG. 5b shows a further embodiment of a sealing knob 44 which comprises a smooth sealing surface 50 and transversely arranged knob sidewalls 52. The outer angles between the sealing surface 50 and the knob sidewalls 52 are about 225° while the angles between the base 46 and the knob sidewalls 52 are about 135°. The obtuse angles of the edges prevent a damage of the materials to be treated.

Figure 5C:
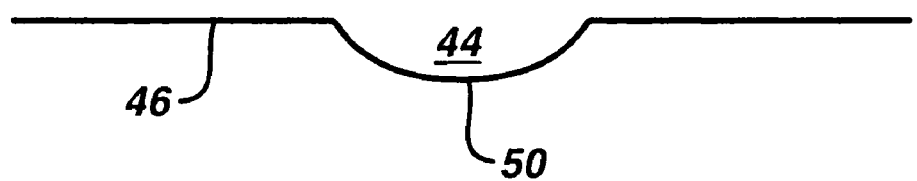

FIG. 5c shows another embodiment of the sealing knob 44 which is ellipsoid-segmentally shaped. These ellipsoid-segmentally shaped sealing knobs 44 securely attach cover 16 and do not significantly damage the cover material.

While the present description has referred to the sealing roller 42 of FIG. 4, the ordinarily skilled practitioner will recognize that the sealing element 40 may also be a substantially planar element capable of reciprocating motion or other physical arrangements that provide appropriate heat and pressure.

Shear Strength Test Method

This test method serves to determine the sealing strength between an absorbent structure and an adjacent material, such as a cover, of a tampon.

1. Test Equipment includes: a tensile testing machine, such as an Instron Model 1011 (50N load transducer, 50 mm pneumatic grips), computer controlled; Software, such as WININ, to operate the testing machine and to describe the results; a balance (0.01 g accurate); and an Eppendorf or similar pipette (adjustable volume to 5 ml).
2. Sample preparation: Tampons are weighed and ten are selected having a target weight±0.1 g. The selected tampons are moistened with appr. 4 ml of water (Eppendorf pipette) and unraveled, if necessary to arrange the absorbent structure and cover in a substantially planar configuration, and the length of sealing area is measured and recorded. Again, if necessary, the absorbent structure is cut to leave only a small amount (at least 2 cm) of structure extending beyond the sealed portion of the cover material to provide a grippable portion for the testing equipment. Absorbent structure and cover end are clamped in the testing machine.
3. Set up the computer-controlled Instron Machine as follows:
   Test Speed: 100 mm/min
   Test Mode: tensile test
   Break action: test stops at breakage and the grips return to their starting position.
   Load range: 20%
   Break detector sensitivity: 20%
   Peak detector sensitivity: 5%

4. Run the test for each sample as follows:
   Adjust distance between testing machine grips to match product to be tested and place the cover material in the upper grip, if applicable.
   Lock mechanical adjustable lower limit stop below lower grip, if appropriate.
   Adjust force display, if necessary.
   Engage test, after force peak is passed the measurement can be stopped with the "STOP" button.
   Record the highest force value as the seal strength.
   Repeat for each sample.

The specification above is presented to aid in the complete and non-limiting understanding of the invention disclosed herein. Since many variations and embodiments of the invention can be made without departing from its spirit and scope, the invention resides in the claims hereinafter appended

What is claimed is:

1. Tampon comprising:
   an absorbent structure
   an apertured film cover thermally bonded to the absorbent structure through a plurality of discrete spots arranged about the surface of the absorbent structure to provide a cumulative cover-to-absorbent bond wherein:
   (a) the plurality of discrete thermally-bonded spots define a bonded area and wherein said bonded spots and the unbonded portions between said spots define a bond region, and said bonded area covers about 5% to about 30% of said bond region:
   (b) the apertured film cover comprises fluid-impervious plastic material in the form of a resilient three-dimensional web exhibiting a fiber-like appearance and tactile impression, wherein the web has first and second surfaces, the first surface having a multiplicity of apertures therein, each of the apertures being defined by a multiplicity of intersecting fiber-like elements interconnected to one another substantially in the plane of the first surface, each of the fiber-like elements exhibiting a cross-section comprising a base portion in the plane of the first surface and a sidewall portion joined to each edge of the base portion, the sidewall portions extending generally in the direction of the second surface of the web, the intersecting sidewall portions being interconnected to one another intermediate the first and the second surfaces of the web, the interconnected sidewall portions terminating substantially concurrently with one another in the plane of the second surface; and
   (c) the cumulative cover-to-absorbent bond has a shear strength of at least about 2N.

2. The tampon of claim 1 wherein the absorbent structure comprises a fibrous web.

3. The tampon of claim 2 wherein the fibrous web comprises synthetic fibers, natural fibers, or a combination thereof.

4. The tampon of claim 1 wherein the apertured film comprises a polymeric material selected from the group consisting of polyolefins, polyesters, polyamides, polyurethanes, polystyrenes, halogenated polymers, and copolymers thereof.

5. The tampon of claim 1 wherein the bonded area covers about 10% to about 25% of the bond region.

6. The tampon of claim 5 wherein the bonded area covers about 15% to about 20% of the bond region.

* * * * *